United States Patent
Shirai et al.

(10) Patent No.: US 7,173,148 B2
(45) Date of Patent: Feb. 6, 2007

(54) PROCESS FOR PRODUCING 1-ACETOXY-3-(SUBSTITUTED PHENYL)PROPENE COMPOUND

(75) Inventors: Masashi Shirai, Ube (JP); Yoshihiro Yoshida, Ube (JP); Shinichiro Sadaike, Ube (JP)

(73) Assignee: Ube Industries, Ltd. (JP)

( * ) Notice: Subject to any disclaimer, the term of this patent is extended or adjusted under 35 U.S.C. 154(b) by 0 days.

(21) Appl. No.: 10/539,785

(22) PCT Filed: Dec. 18, 2003

(86) PCT No.: PCT/JP03/16277

§ 371 (c)(1),
(2), (4) Date: Jun. 17, 2005

(87) PCT Pub. No.: WO2004/054997

PCT Pub. Date: Jul. 1, 2004

(65) Prior Publication Data

US 2006/0069273 A1    Mar. 30, 2006

(30) Foreign Application Priority Data

Dec. 18, 2002  (JP)  ............................ 2002-367031
Mar. 14, 2003  (JP)  ............................ 2003-069733
Sep. 9, 2003   (JP)  ............................ 2003-316336

(51) Int. Cl.
C07C 67/02    (2006.01)
(52) U.S. Cl. ...................................... 560/261
(58) Field of Classification Search ................. 560/261
See application file for complete search history.

(56) References Cited

U.S. PATENT DOCUMENTS 3,023,247 A *  2/1962  Scriabine ..................... 568/433
4,389,527 A    6/1983  Valentine et al.

FOREIGN PATENT DOCUMENTS

JP    55-141437 A    11/1980

OTHER PUBLICATIONS

Igor Scriabine, No. 185 Nouveau procede de preparation des aldehydes dihydrocinnamiques, Bulletin de la Societe chimique de France, Jun. 1961, pp. 1194-1198.*
David A Evans, J. Stephen Clark, Rainer Metternich, Vance J. Novack, and George S. Sheppard Diastereoselective Aldol Reactions Using beta keto Imide Derived Enolates. A Versatile Approach to the Assemblage of Polypropionate Systems J. Am. Chem. Soc. 1990, 112, 866-868.*

Igor Scriadine New Method for Preparation of Dihydrocinnamaldehydes Bull Soc Chim de France, Section 6, Jun. 1961 pp. 1194-1198 (Traslation provided).*
Igor Scriabine, *No. 185.-Nouveau procédé de préparation des aldéhydes dihydrocinnamiques*, Bulletin de la Société chimique de France, Jun. 1961, pp. 1194-1198.

* cited by examiner

Primary Examiner—Samuel A Barts
Assistant Examiner—Lalitha Nagubandi
(74) Attorney, Agent, or Firm—DLA Piper US LLP

(57) ABSTRACT

The compounds represented by the formula (I) are produced by reacting benzene compound of the formula (IV) or (V) with alkenylidene diacetate of the formula (VI) in the presence of a catalyst comprising one or more members selected from (a) halogenated boron compounds,
(b) triflate compounds of Group 11 elements,
(c) halogenated compounds of Group 12 elements, and
(d) triflate and halogenated compounds of tin and atomic numbers 58 and 66 to 71 elements.

$R^1$, $R^2$=H or C1–C10 alkyl group
A=Substituted phenyl group corresponding to a compound of formula (IV) or (V),
$R^3$, $R^4$=H or C1–C4 alkyl group, m=0 or 1–4, n=1 to 5, k=1 or 2.

15 Claims, No Drawings

PROCESS FOR PRODUCING 1-ACETOXY-3-(SUBSTITUTED PHENYL)PROPENE COMPOUND

TECHNICAL FIELD

The present invention relates to a process for producing a 1-acetoxy-3-(substituted phenyl)propene compound. More particularly, the present invention relates to a process for producing a 1-acetoxy-3-(substituted phenyl)propene compound having a phenyl group substituted with a substituent group, for example, an alkoxy group or an alkylenedioxy group, and located in the 3-position of the propene compound.

The 1-acetoxy-3-(substituted phenyl)propene compound produced by the process of the present invention is useful as an intermediate material for perfumes, pharmaceuticals, agricultural chemicals and other organic synthetic chemicals.

BACKGROUND ART

Bull, Soc, Chim, Frame, 1961, p1195–1198, discloses, as a process for synthesizing a 1-acetoxy-3-(substituted phenyl)propene compound, a process for synthesizing 1-acetoxy-3-(3,4-dimethoxyphenyl)propene by reacting 1,2-dimethoxybenzene with an alkenylidene diacetate in the presence of titanium tetrachloride activated with a boron trifluoride-ether complex. This literature reported that the yield of the target compound produced by this process was 62%, which was unsatisfactory. The inventors of the present invention tried to trace the process of the above-mentioned literature, and as a result, found that the yield of the target compound was only 12%, a plurality of by-products were produced, and the resultant product mixture liquid exhibited a brown color (refer to Comparative Example 3 of the present application). Also, it was confirmed that titanium tetrachloride, used for the process of the literature, was a chemically unstable compound to such an extent that this compound is decomposed by moisture in the atmospheric air, and thus complicated and meticulous care is needed in handling this compound.

Further, the inventors of the present invention tried to apply the process of the literature to the reaction of 3,4-methylenedioxy benzene with an alkenylidene diacetate and found that the titanium tetrachloride activated by boron trifluoride-ether complex caused a decomposition reaction of 3,4-methylenedioxybenzene to be promoted, and the yield of the target compound was 43% and unsatisfactory (refer to Comparative Example 1 of the present application). Furthermore, the inventors of the present invention tried to effect the reaction by using titanium tetrachloride in an amount of 0.1 mole per mole of alkenylidene diacetate, to control or prevent the decomposition of 3,4-methylenedioxybenzene. As a result, the yield of the target compound decreased to 9.8% (refer to Comparative Example 2 of the present application).

Japanese Unexamined Patent Publication No. 55–141437 discloses a process for producing 1-acetoxy-2-methyl-3-(4-t-butylphenyl)propene by reacting t-butylbenzene with methacrolein and acetyl chloride in the presence of a stoichiometric amount of a Lewis acid. In this process, when titanium tetrachloride was used as Lewis acid, the yield of the target compound was 46.2%, and when boron trifluoride-ether complex was employed as a Lewis acid, the yield of the target compound was 2.3%. In each of the above-mentioned cases, the target compound yield was low and unsatisfactory.

SUMMARY

We provide a process for producing a 1-acetoxy-3-(substituted phenyl)propene compound useful, as an intermediate material, for perfumes, pharmaceuticals, agricultural chemicals and other organic synthetic chemicals with high efficiency and an easy process.

The process for producing a 1-acetoxy-3-(substituted phenyl)propene compound represented by the general formula (I):

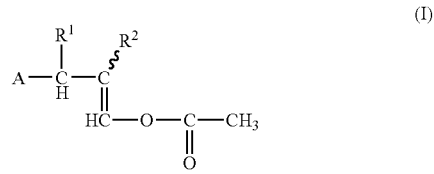

in which formula (I), $R^1$ and $R^2$, respectively and independently from each other, represent a member selected from the groups consisting of a hydrogen atom and alkyl groups having 1 to 10 carbon atoms, $R^1$ and $R^2$ may form, together with carbon atoms located in the 2- and 3-positions of the propene group, a cyclic group; and A represents a member selected from a group of substituted phenyl groups represented by the formulae (II) and (III):

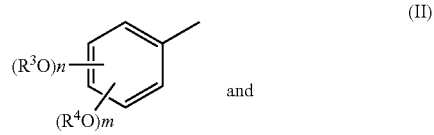

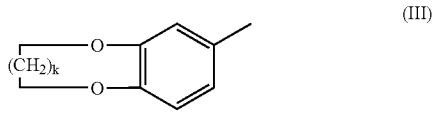

wherein $R^3$ and $R^4$, respectively and independently from each other, represent an alkyl group having 1 to 4 carbon atoms, m represents an integer of 0 or 1 to 4, n represents an integer of 1 or 5 and k represents an integer of 1 or 2, comprises reacting a benzene compound selected from those represented by the general formulae (IV) and (V):

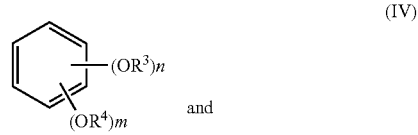

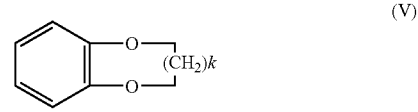

in which formula (IV) and (V), $R^3$ and $R^4$ and n, m and k are as defined above, with an alkenylidene diacetate compound represented by the general formula (VI):

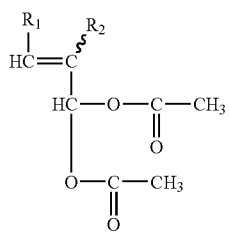

in which formula (VI), $R^1$ and $R^2$ are as defined above, in the presence of a catalyst comprising at least one compound selected from the group consisting of (a) halogenated boron compounds, (b) triflate compounds of Group 11 elements of the Periodic Table, (c) halogenated compounds of Group 12 elements of the Periodic Table, and (d) triflate compounds and halogenated compounds of tin and lanthanoid elements of atomic numbers 58 and 66 to 71.

The benzene compounds represented by the formula (IV) are preferably selected from the group consisting of anisole, veratrol, hydroquinone dimethylether, Pyrogallol tri-methylether and hydroxyhydroquinone trimethylether.

The benzene compounds represented by the formula (V) are preferably selected from the group consisting of 1,2-methylenedioxybenzene and 1,2-ethylenedioxybenzene.

The alkenylidene diacetate is preferably selected from the group consisting of 3,3-diacetoxy-2-methylepropene,3,3-diacetoxy propene, 3,3 -diacetoxy- 1-methyipropene,3,3-diacetoxy-2-ethyl propene,3,3-diacetoxy-1-ethyipropene, and 3,3-diacetoxy-1-ethyl-2-methyl-propene.

The reaction is preferably carried out in a molar ratio of the benzene compound to the alkenylidene diacetate compound of 1:1 to 50:1.

The catalyst is preferably present in an amount of 0.005 to 1 mole per mole of the alkenylidene diacetate compound.

The halogenated boron compounds (a) usable for the catalyst are preferably selected from boron fluorides, boron trifluoride-diethylether complexes, borontrifluoride-tetrahydrofuran complexes, boron trifluoride-acetic acid complex salt, boron trifluoride dehydrate, and boron trifluoride-n-butylether complexes.

The triflate compounds (b) of Group II elements of the Periodic Table usable for the catalyst are preferably selected from the group consisting of copper triflate and silver triflate.

The halogenated compounds (c) of Group 12 elements of the Periodic Table usable for the catalyst are preferably selected from the group consisting of zinc fluoride, zinc chloride, zinc bromide, zinc iodide, cadmium fluoride, cadmium chloride, cadmium bromide, cadmium iodide, hydrogen fluoride, mercury chloride, mercury bromide, and mercury iodide.

The triflate and halogenated compounds (d) of tin and lanthanoid elements of atomic numbers 58 and 66 to 71 are preferably selected from the group consisting of triflates, fluorides, chloride, bromides, and iodide of tin, cerium, dysprosium, holmium, erbium, thulium, ytterbium and lutetium.

The reaction is preferably carried out in an atmosphere consisting of a non-reactive gas to the above-mentioned compounds of the formulae (IV), (V) and (VI), the above-mentioned catalyst and the resultant reaction products.

The compounds of the formula (I) are preferably selected from the compounds represented by the general formula (VII):

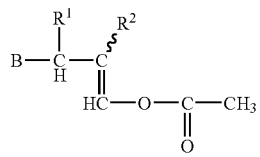

in which formula (VII), $R^1$, $R^2$ are as defined above, B represents a member selected from a group of substituted phenyl groups represented by the formulae (VIII) and (IX):

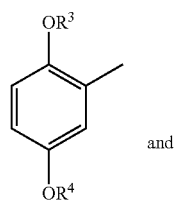

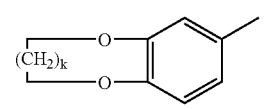

in which formulae (VIII) and (IX), $R^3$ and $R^4$ and k are as defined above.

The compounds represented by the formula (VII) are new compounds.

The compound of the formula (I) is preferably selected from 1-acetoxy-3-(3,4-C1 to C2 alkylene dioxyphenyl)propenes represented by the formulae (X) and (XI):

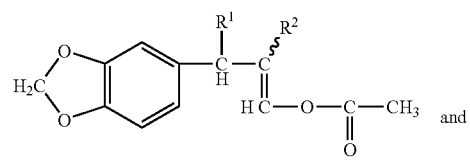

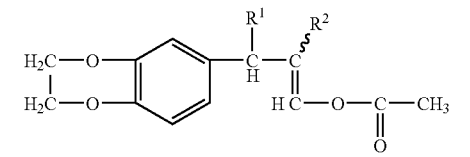

The compounds represented by the formulae (X) and (XI) are new compounds.

Preferably in the formulae (X) and (XI), $R^1$ represents a hydrogen atom and $R^2$ represents a methyl group.

The compound of the formula (I) is preferably selected from the groups consisting of 1-acetoxy-2-methyl-3-(3,4-methylenedioxyphenyl)propene, 1-acetoxy-2-methyl-3-(3, 4ethylenedioxyphenyl)propene, 1-acetoxy-2-methyl-3-(4- methoxyphenyl) propene, 1-acetoxy-yl-3-(2,5-dimethoxyphenyl)) propene, 1-acetoxy-2-methyl-3-(3,4-dimethoxyphenyl)propene.

Among the compounds, 1-acetoxy-2-methyl-3-(3,4-methylenedioxyphenyl) propene, 1-acetoxy-2-methyl-3-(3,4-ethylenedioxyphenyl)propene, and 1-acetoxy-2-methyl-3-(2,5-dimethoxyphenyl)propene are new compounds.

The Periodic Table is based on the 18 Groups-Type Elemental Periodic Table, IUPAC and Nomenclature in Inorganic Chemistry, 1990 Rule.

Also, the term "triflate" refers to trifluoromethanesulfonate.

DETAILED DESCRIPTION

The 1-acetoxy-3-(substituted phenyl)propene compound produced by the process is represented by the above-mentioned general formula (I) and includes a plurality of types of stereoisomers due to asymmetric carbon atoms and/or a double bond contained in the molecule of the compound.

The process for producing 1-acetoxy-3-(substituted phenyl)propene compound comprises the step of reacting at least one member selected from a group of benzene compounds represented by the above-mentioned general formulae (IV) and (V) with an alkenylidene diacetate represented by the general formula (VI) in the presence of a specific catalyst which will be illustrated in detail hereinafter. The benzene compounds represented by the formulae (IV) and (V) correspond to the substituted phenyl groups represented by the general formula (II) and (III), and the alkenylidene diacetate of the general formula (VI) corresponds to a 1-acetoxypropene group bonded to the A group contained in the general formula (I).

The specific catalysts for the process comprises at least one member selected from the group consisting of:

(a) halogenated boron compounds,
(b) triflate compounds of Group II elements of the Periodic Table,
(c) halogenated compounds of Group 12 elements of the Periodic Table, and (d) triflate compounds and halogenated compounds of tin and lanthanoid elements of atomic numbers 58 and 66 to 71.

In the process, the benzene compound represented by the general formula (IV) is preferably selected from anisole, veratrole, hydroquinonedimethylether, pyrogalloltrimethylether, and hydroxyl hydroquinonetrimethylether. Among them, anisol and veratrol are particularly preferably used. These compounds may be of a common trade grade.

Also, the benzene compound represented by the general formula (V) is preferably selected from 1,2-methylenedioxybenzene and 1,2-ethylenedioxybenzene.

Further, the alkenylidene diacetate represented by the general formula (VI) is preferably selected from the group consisting of 3,3-diacetoxy-2-methylpropene, 3,3-diacetoxy-propene, 3,3-diacetoxy-1-methylpropene, 3,3-diacetoxy-2-ethylpropene, 3,3-diacetoxy-1-ethylpropene and 3,3-diacetoxy-1-ethyl-2-methylpropene. These compounds may be in trade grade and, optionally may be prepared with an α,β-unsaturated aldehyde and acetic anhydride in accordance with the process disclosed in Bull, Soc, Chim, Frame, 1961, p1194 to 1198. These compounds include isomers.

In the alkenylidene diacetate represented by the general formula (VI), groups $R^1$ and $R^2$ may be bonded to each other to form, together with the carbon atoms in the 2- and 3-positions of the propene group, a cyclic group.

The cyclic group is preferably a cyclopentane or cyclohexane group, more preferably a cyclohexane group.

The α,β-unsaturated aldehyde usable for the preparation of the alkenylidene diacetate preferably include acrolein, methacrolein, crotonaldehyde, α,β-dimethylacrolein, α-ethylacrolein, β-ethylacrolein, β-propylacrolein and α-cyclohexylacrolein, more preferably acrolein, methacrolein and crotonaldehyde, still more preferably methacrolein.

The halogenated boron compound (a) for the catalyst usable for the process includes, for example, boron fluoride, boron trifluoride-diethylether complex, boron trifluoride-tetrahydrofuran complex, boron trifluoride-acetic acid complex salt, boron trifluoride-dihydrate and boron trifluoride-n-butylether complex. Among them, boron trifluoride-ether complex and boron trifluoride-acetic acid complex salt are more preferably employed. These compounds may be of a trade grade.

The triflate compound of the Group 11 elements for the catalyst is preferably selected from copper triflate and silver triflate.

The halogenated compounds (c) of the Group 12 elements for the catalyst preferably include zinc fluoride, zinc chloride, zinc bromide, zinc iodide, cadmium fluoride, cadmium chloride, cadmium bromide, cadmium iodide, mercury fluoride, mercury chloride mercury bromide and mercury iodide. Among them, the halogenated compounds of zinc are more preferably employed, and zinc chloride is still more preferably employed.

The triflate compounds and halogenated compounds (d) of tin and atomic number 58 and 66 to 71 lanthanoid elements preferably include tin triflate, tin fluoride, tin chloride, tin bromide, tin iodide, cerium fluoride, cerium chloride, cerium bromide, cerium iodide, cerium triflate, dysprosium fluoride, dysprosium chloride, dysprosium bromide, dysprosium iodide, dysprosium triflate, holmium fluoride, holmium chloride, holmium bromide, holmium iodide, holmium triflate, erbium fluoride, erbium chloride, erbium bromide, erbium iodide, erbium triflate, thulium fluoride, thulium chloride, thulium bromide, thulium iodide, thulium triflate, ytterbium fluoride, ytterbium chloride, ytterbium bromide, ytterbium iodide, ytterbium triflate, lutetium fluoride, lutetium chloride, lutetium bromide, lutetium iodide, lutetium triflate, and hydrates of the above-mentioned compounds. Among them, tin chloride, tin triflate, erbium triflate, thulium triflate, ytterbium chloride, ytterbium triflate and lutetium triflate are more preferably employed. Still more preferably, tin chloride and ytterbium chloride are employed.

In the process, the catalyst is preferably employed in an amount of 0.005 to 1 mole preferalby 0.01 to 0.5 mole, still more preferably 0.01 to 0.2 mole, per mole of the alkenylidene diacetate. If the catalyst is used in an amount of more than 1 mole, complicated procedures may be needed for recovery, decomposition and disposal of the catalyst after the reaction is completed, and may cause the practice of the process in the industrial scale to be inconvenient. Also, if the amount of the catalyst is less than 0.005 mole, the reaction may not be completed within a practical time, for example, within 24 hours.

The reaction in the may be carried out in a solvent medium. Usually, the reaction is preferably not carried out in a solvent medium. For the solvent, aromatic hydrocarbons, for example, benzene and toluene, xylene; halogenated aromatic hydrocarbons, for example, chlorobenzene; and halogenated aliphatic hydrocarbons, for example, methylene chloride and dichloroethane, may be employed.

The reaction temperature for the process can be appropriately established in response to the types and concentrations of the starting compounds and catalysts. Usually, the reaction is carried out at a temperature of −10 to 80° C., more preferably 0 to 60° C. The reaction time for the process can be appropriately established in consideration of the types and concentrations of the starting compounds and catalysts and the reaction temperature. Usually, the reaction time is preferably in the range of from 0.5 to 24 hours, more preferably 0.5 to 12 hours.

There is no specific limitation to the type of the reaction atmosphere for the process. Usually, the reaction of the process is carried out in a gas nonreactive to the starting compounds (namely, the compounds of the general formulae (I) and (II), the catalyst and the resultant products, for example, a gas atmosphere or flow comprising at least one gas selected from nitrogen gas and inert gases, for example, argon gas. The reaction is usually carried out at the ambient atmospheric pressure. However, the reaction pressure is not limited to that mentioned above.

The 1-acetoxy-3-(substituted phenyl)propene compound produced in accordance with the process is usually refined by separating the compound from the resultant reaction mixture liquid after the reaction is completed by a usual separate-recovery procedure, for example, an extraction, a concentration and a filtration and then optionally by applying a refining procedure, for example, a distillation, recrystallization and various chromatographies, to the separate-recovered fraction.

In the general formula (I) representing the 1-acetoxy-3-(substituted phenyl)propene compound produced by the process, $R^1$ and $R^2$ represent a hydrogen atom or a C1–C10 alkyl group, and preferably, at least one of $R^1$ and $R^2$ represents a C1–C10 alkyl group. The C1–C10 alkyl groups represented by $R^1$ and $R^2$ include methyl, ethyl, propyl, butyl, pentyl, hexyl, heptyl, octyl, nonyl and decyl groups. These groups respectively include a plurality of isomers. The alkyl group represented by $R^1$ and $R^2$ is preferably a methyl group.

In the general formula (I), the alkyl groups represented by $R^1$ and $R^2$ may be bonded (or fused) at the terminals thereof to each other to form, together with the carbon atoms located in the 1- and 2-positions of the propene group, a cyclic group. The cyclic group is preferably, for example, a cyclopentane or cyclohexane group, more preferably a cyclohexane group.

In the compound of the general formula (I), $R^3$ and $R^4$ in the substituted phenyl group (A) represented by the general formulae (II) and (III), respectively and independently from each other represent a C1–C4 alkyl group, m represents an integer of 0 (zero) or 1 to 4, n represents an integer of 1 to 5, k represents an integer of 1 or 2. The C1–C4 alkyl groups represented by $R^3$ and $R^4$ include methyl, ethyl, propyl and butyl groups, and each alkyl group includes a plurality of isomers. The C1–C4 alkyl groups preferably selected from methyl, ethyl, n-propyl isopropyl, n-butyl, isobutyl and sec-butyl Among the compounds of the general formula (I) produced by the process, the 1-acetoxy-3-(substituted phenyl) propene compounds represented by the general formula (VII):

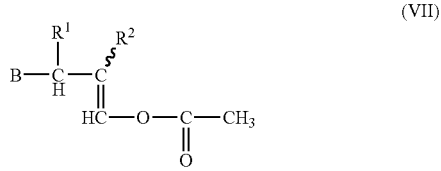

(VII)

in which formula (VII), $R^1$, $R^2$ are as defined above, B represents a member selected from a group of substituted phenyl groups represented by the formulae (VIII) and (IX):

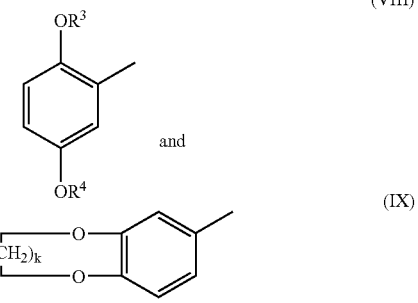

in which formulae (VIII) and (IX), $R^3$ and $R^4$ and k are as defined above, are novel compounds.

In the case where the A in the general formula (I) represents the substituted phenyl groups of the general formula (III), the 1-acetoxy-3-(substituted phenyl)propene compounds represented by the general formula (I) is preferably selected from the 1-acetoxy-3-(3,4-C1–C2alkylenedioxy-phenyl)propenes represented by the general formulae (X) and (XI). In this case, in the general formulae (X) and (XI), preferably, $R^1$ represents a hydrogen atom and $R^2$ represents a methyl group.

Also, in the general formula (I) representing the 1-acetoxy-3-(substituted phenyl)propene compounds, in the case where A represents the substituted phenyl groups represented by the general formula (II), the substituted phenyl group (II) preferably selected from 4-methoxyphenyl group, 2,5-dimethoxyphenyl group and 3,4-dimethoxyphenyl group.

Accordingly, the 1-acetoxy-3-(substituted phenyl)propene compounds represented by the general formula (I) are preferably selected from the group consisting of 1-acetoxy-2-methyl-3-(3,4-methylenedioxyphenyl)propene, 1-acetoxy-2-methyl-3-(3,4-ethylene-dioxyphenyl) propene, 1-acetoxy-2-methyl-3-(4-methoxyphenyl)propene, 1-acetoxy-2-methyl-3-(2,5-dimethoxyphenyl)propene, and 1-acetoxy-2-methyl-3-(3,4-dimethoxyphenyl)propene.

EXAMPLES

Selected aspects of the invention will be further illustrated by the following examples which are not intended to limit the scope of the appended claims in any way.

In the examples, the yield of 1-acetoxy-2-methyl-3-(substituted phenyl)propene was calculated on the basis of mass of 3,3-diacetoxy-2-methylpropene employed.

Example 1

In an argon gas atmosphere at a temperature of 20° C., a 20 ml flask was charged with a mixed solution of 6.83 g (56.0 m moles) of 1,2-methylenedioxybenzene and a solution 1.05 g (5.6 m moles) of 3,3-diacetoxy-2-methylpropene in a purity degree of 91.8% by mass, and the mixed solution was mixed with 74 mg (0.52 m mole) of boron trifluoride-diethylether complex. The resultant mixture was stirred at a temperature of 23° C. for one hour to provide a reaction liquid. The reaction liquid was mixed with 50 ml of ethyl acetate, and a resultant organic phase layer formed in the reaction liquid is separated and collected, washed three times with water in an amount of 50 ml, and dried with anhydrous sodium sulfate to remove the solvent. The resultant residue was refined by a column chromatography on silica gel using a solvent ethyl acetate/n-hexane mixture in a mixing ratio by volume of 1/13, the target 1-acetoxy-2- methyl-3-(3,4-methylenedioxyphenyl)propene was eluted and collected in an amount of 1.15 g in the form of white crystals. The resultant target compound was obtained in an isolation yield of 88%.

The physical property data of 1-acetoxy-2-methyl-3-(3,4-methylenedioxyphenyl)propene are shown below.

$^1$H-NMR (300 MHz, CDCl$_3$) δ=1.56 (3H, d, J=1.5 Hz), 2.15 (3H, s), 3.18 (2H, s), 5.92 (2H, s), 6.63 (1H, dd, J=7.8 Hz, J=1.5 Hz), 6.67 (1H, d, J=1.5 Hz), 6.72 (1H, d, J=7.8 Hz), 7.02 (1H, q, J=1.5 Hz).

$^{13}$C-NMR (75.5 MHz, CDCl$_3$) δ=13.43, 20.78, 40.05, 100.86, 108.10, 109.10, 121.31, 121.70, 131.24, 132.79, 146.08, 147.69, 168.26.

Elemental Analysis

|  | C (%) | H (%) |
| --- | --- | --- |
| Calculated for C$_{13}$H$_{14}$O$_4$ | 66.66 | 6.02 |
| Found | 66.71 | 6.16 |

Example 2

In an argon gas atmosphere at a temperature of 20° C., a 20 ml flask was charged with a mixed solution of 6.83 g (55.97 m moles) of 1,2-methylenedioxybenzen and 0.96 g (4.88 m moles) of 3,3-diacetoxy-2-methylpropene in a purity degree of 88.0% by mass, and the mixed solution was mixed with 77 mg (0.54 m mole) of boron trifluoride-diethylether complex. The resultant mixture was stirred at a temperature of 23° C. for one hour to provide a reaction liquid. The reaction liquid was mixed with 100 ml of acetonitrile.

The resultant reaction liquid was subjected to a high performance liquid chromatographic analysis in accordance with an absolute calibration curve method. In the result of the analysis, the yield of 1-acetoxy-2-methyl-3-(3,4-methylenedioxyphenyl)propene was 97.1%. Also, the reaction liquid contained non-reacted 1,2-methylenedioxybenzene in an amount of 5.86 g.

Examples 3 to 6

In each of Examples 3 to 6, the same reaction and analysis as in Example 2 were carried out, except that a 1,2-methylenedioxybenzene, 3,3-diacetoxy-2-methylpropene and boron trifluoride-ether complex were employed in the amounts as shown in Table 1 and the reaction temperature and the reaction time were changed as shown in Table 1.

The reaction results are shown in Table 1.

Comparative Example 1

In an-argon gas atmosphere, a 25 ml three necked flask was charged with 1.28 g (6.7 m moles) of titanium tetrachloride and then with 0.017 g (0.12 m mole) of boron trifluoride-diethylether complex. In the resultant mixture, 3.27 g (26.8 m moles) of 1,2-methylenedioxybenzene were added dropwise over a time of 60 minutes at an internal temperature of the flask of 8 to 12° C. and then a mixture 1.05 g (6.1 m moles) of 3,3-diacetoxy-2-methylpropene in a purity degree of 100% by mass with 0.75 g (6.1 m moles) of 1,2-methylenedioxybenzene was added dropwise over 15 minutes. The resultant mixture was stirred at an internal temperature of 8 to 10° C for 30 minutes, then mixed with 10 ml of a 6N-hydrochloric acid and 10 ml of dichloromethane and the resultant mixture was stirred for 30 minutes. From the resultant mixture, the resultant insoluble fraction was separated by filtration, the resultant filtrate was mixed with dichloromethane to apply an extraction treatment to the filtrate. The resultant organic layer was separated and collected, washed with water, further washed with a saturated aqueous sodium chloride solution and then dried on anhydrous sodium sulfate. The resultant liquid material was subjected to filtration and concentration treatments. A crude product was obtained in an amount of 3.16 g. The crude product was subjected to a high performance liquid chromatographic analysis in accordance with the absolute calibration curve method. In the analysis results, the yield of the target 1-acetoxy-2-methyl-3-(3,4-methylenedioxyphenyl)propene was 43.1% and the resultant reaction liquid contained non-reacted 1,2-methylenedioxybenzene in an amount of 1.40 g.

Comparative Example 2

In an argon gas atmosphere, a three necked flask having a capacity of 25 ml was charged with 0.10 g (0.5 m moles) of titanium tetrachloride and then 0.94 g (5.0 m moles) of 3,3-diacetoxy-2-methylpropene in a purity degree of 91.7% by mass was placed dropwise into the flask at an internal temperature of 4 to 5° C. To the resultant mixture, 6.11 g (50.0 m moles) of 1,2-methylenedioxybenzene were added dropwise. The temperature of the resultant reaction mixture was raised to 23° C., and the resultant mixture was stirred for 18 hours. The resultant reaction liquid was mixed with 20 g of ethyl alcohol. The resultant liquid material was subjected to a high performance liquid chromatographic analysis in

TABLE 1

|  |  | Compound 1 (mmol)$^{(*)1}$ | Compound 2 (mmol)$^{(*)2}$ | BF$_3$.Et$_2$O (mmol)$^{(*)4}$ | Reaction temperature (° C.) | Reaction time (h) | Yield of compound 3 (%)$^{(*)3}$ |
| --- | --- | --- | --- | --- | --- | --- | --- |
| Example | 3 | 27.99 | 5.55 | 0.54 | 0 | 2 | 84.6 |
|  | 4 | 27.94 | 5.55 | 0.56 | 23 | 1 | 89.3 |
|  | 5 | 27.94 | 5.55 | 0.27 | 23 | 3 | 86.8 |
|  | 6 | 55.95 | 5.61 | 5.58 | 23 | 0.5 | 93.8 |

Note:
$^{(*)1}$Compound 1: 1,2-methylenedioxybenzen
$^{(*)2}$Compound 2: 3,3-diacetoxy-2-methylpropene
$^{(*)3}$Compound 3: 1-acetoxy-2-methyl-3-(3,4-methylenedioxyphenyl) propene
$^{(*)4}$BF$_3$ 19 Et$_2$O: Boron triflate-diethylethel complex accordance with the absolute calibration curve method. In the analysis results, the yield of the target 1-acetoxy-2-methyl-3-(3,4-methylenedioxyphenyl)propene was 9.8%.

Example 7

In an argon gas atmosphere at a temperature of 20° C., a flask having a capacity of 25 ml was charged with a mixed solution of 6.83 g (56.0 m moles) of 1,2-methylenedioxybenzen with 152 mg (1.12 m moles) of zinc chloride. Then, the mixed solution was mixed with 0.96 g (5.60 m moles) of 3,3-diacetoxy-2-methylpropene in a content of 100% by mass. The mixed solution was stirred at an internal temperature of 23° C. for 3 hours to provide a reaction liquid. The reaction liquid was mixed with 85 ml of acetonitrile. The resultant mixed liquid was subjected to a high performance liquid chromatography to analyze the mixed liquid in accordance with the absolute calibration curve method. In the analysis result, the yield of the target 1-acetoxy-2-methyl-3-(3,4-methylenedioxyphenyl)propene was 88.3%.

The resultant reaction liquid contained 6.06 g of non-reacted 1,2-methylenedioxybenzene.

Example 8

In an argon gas atmosphere at a temperature of 20° C., a flask having a capacity of 25 ml was charged with a mixed solution of 2.44 g (20.0 m moles) of 1,2-methylenedioxybenzen and a 72 mg (0.20 m mole) of copper triflate, and the mixed solution was mixed with 0.38 g (2.0 m moles) of 3,3-diacetoxy-2-methylpropene in a content of 100% by mass, and the mixed solution was stirred at an internal temperature of 22° C. for 6 hours. The resultant mixture was mixed with ethanol in an amount of 10 ml.

The resultant reaction liquid was subjected to a high performance liquid chromatographic analysis in accordance with the absolute calibration curve method. In the analysis results, the yield of 1-acetoxy-2-methyl-3-(3, 4-methylenedioxyphenyl)propene was 84%, and the reaction liquid contained 2.17 g of non-reacted 1,2-methylenedioxybenzene.

Examples 9 to 11

In each of Examples 9 to 11, the same reaction as in Example 7 was carried out, with the following exceptions.

The amounts of 1,2-methylenedioxybenzene, 3,3-diacetoxy-2-methylpropene and zinc chloride and the reaction time were changed to as shown in Table 2. The results are shown in Table 2.

Example 12

In an argon gas atmosphere, a four necked flask having a capacity of 200 ml was charged with 19.22 g (100 m moles) of 3,3-diacetoxy-2-methylpropene having a purity degree of 89.6% by mass and 108.14 g (1.0 mole) of anisol. Then, the resultant mixture was mixed with 1.42 g (10 m moles) of boron trifluoride-diethylether complex at an internal temperature of 24° C. for 2 minutes. The mixture was stirred at an internal temperature of 24 to 25° C. for one hour to cause the mixed propene compound and anisol to react with each other. After the reaction was completed, the resultant reaction liquid was washed two times with 20 ml of water and further with 20 ml of saturated aqueous sodium chloride solution. The resultant reaction liquid was subjected to a layer separation treatment, the resultant organic layer was removed by a distillation under reduced pressure (20 mmHg, 55 to 57° C.), the resultant residue was refined by a chromatography on silica gel using an eluting solvent:hexane/ethyl acetate mixture in a mixing volume ratio: 10/1. As a colorless liquid fraction, the target 1-acetoxy-2-methyl-3-(4-methoxyphenyl)propene was obtained in a yield of 93.4% in an amount of 20.58 g.

Example 13

In an argon gas atmosphere, a three necked flask having a capacity of 25 ml was charged with 1.92 g (10 m moles) of 3,3-diacetoxy-2-methylpropene having a purity degree of 89.6% by mass and 13.82 g (100 m moles) of hydroquinone dimethylether. Then, the resultant mixture was mixed with 0.14 g (1 m mole) of boron trifluoride-diethyl ether complex at an internal temperature of 54° C. over a time of one minute. The mixture was stirred at an internal temperature of 53 to 54° C. for one hour to cause the mixed compounds to react with each other. After the reaction was completed, the resultant reaction liquid was mixed with 150 ml of ethyl acetate and washed two times with 20 ml of saturated aqueous sodium chloride solution. The resultant reaction liquid was subjected to a layer separation treatment, the resultant organic layer was distilled under reduced pressure (20 mmHg, 55 to 57° C.), the resultant residue was refined by a chromatography on silica gel using an eluting solvent: hexane/ethyl acetate mixture in a mixing ratio by volume of 10/1. As a colorless liquid fraction, the target 1-acetoxy-2-methyl-3-(2,5-dimethoxyphenyl)propene was obtained in a yield of 77.4% in an amount of 1.94 g in the form of a colorless solid.

The physical property data of 1-acetoxy-2-methyl-3-(2, 5-dimethoxyphenyl)propene are shown below.

TABLE 2

| | | Compound 1 (mmol)[*]1 | Compound 2 (mmol)[*]2 | Zinc Chloride (mmol) | Reaction temperature (° C.) | Reaction time (h) | Yield of compound 3 (%)[*]3 |
|---|---|---|---|---|---|---|---|
| Example | 9 | 55.97 | 5.95 | 0.54 | 23 | 6 | 82.1 |
| | 10 | 55.88 | 5.58 | 2.81 | 23 | 1 | 90.0 |
| | 11 | 27.96 | 5.62 | 1.16 | 23 | 2 | 81.9 |

Note:
[*]1Compound 1: 1,2-methylenedioxybenzene
[*]2Compound 2: 3,3-diacetoxy-2-methylpropene
[*]3Compound 3: 1-acetoxy-2-methyl-3-(3,4-methylenedioxyphenyl) propene $^1$H NMR (300 MHz, CDCl$_3$) δ:1.63 (3H, d, J=1.5 Hz), 2.13 (3H, s), 3.26 (2H, s), 3.75 (3H, s), 3.77 (3H, s), 6.70–6.74 (2H, m), 6.78 (1H, d, J=9.6 Hz), 6.99 (1H, q, J=1.5 Hz).

$^{13}$C NMR (75.5 MHz, CDCl$_3$) δ:13.75, 20.76, 33.73, 55.66, 56.06, 111.57, 120.58, 128.67, 131.58, 151.98, 153.55, 168.17.

HRMS (EI)(M+)

Calculated for C$_{14}$H$_{18}$O$_4$: 250.1205

Found: 250.1198

Example 14

In an argon gas atmosphere, a three necked flask having a capacity of 25 ml was charged with 1.92 g (10 m moles) of 3,3-diacetoxy-2-methylpropene having a purity degree of 89.6% by mass and 13.82 g (100 m moles) of hydroquinone dimethylether. Then, the resultant mixture was mixed with 0.14 g (1 m mole) of boron trifluoride-ether complex at an internal temperature of 54° C. for one minute. The mixture was stirred at an internal temperature of 53 to 54° C. for one hour to cause the mixed compounds to react with each other. After the reaction was completed, the resultant reaction liquid was subjected to a quantitative analysis using a high performance liquid chromatography. It was confirmed that the target 1-acetoxy-2-methyl-3-(2,5-dimethoxyphenyl)propene was produced in an amount of 2.16 g (yield: 86.0%).

Example 15

In an argon gas atmosphere, a four necked flask having a capacity of 100 ml was charged with 69.2 g (500 m moles) of 1,2-dimethoxybenzene and 9.61 g (50 m moles) of 3,3-diacetoxy-2-methylpropene having a purity degree of 89.6% by mass. Then, the resultant mixture was mixed with 1.36 g (10 m moles) of zinc chloride at an internal temperature of 25 to 26° C. The mixture was stirred at an internal temperature of 25 to 26° C. for 1.5 hours to cause the mixed compounds to react with each other. After the reaction was completed, the resultant reaction liquid was washed three times with 50 ml of saturated aqueous sodium chloride solution. The resultant reaction liquid was subjected to a layer separation treatment, the resultant organic layer was collected and subjected to a distillation under reduced pressure (8 to 10 mmHg, 80 to 84° C.), the resultant residue was refined by a chromatography on silica gel using an elusion solvent:hexane/ethyl acetate mixture in a mixing ratio by volume of 10/1. The target 1-acetoxy-2-methyl-3-(3,4-dimethoxyphenyl)propene was obtained in a yield of 95.1% in an amount of 11.9 g in the form of a colorless liquid.

Example 16

In an argon gas atmosphere, a three necked flask having a capacity of 25 ml was charged with 13.82 g (100 m moles) of 1,2-dimethoxybenzene and 1.87 g (10 m moles) of 3,3-diacetoxy-2-methylpropene having a purity degree of 92.0% by mass. Then, the resultant mixture was mixed with 0.142 g (1 m mole) of boron trifluoride-ether complex at an internal temperature of 18 to 19° C. The mixture was stirred at an internal temperature of 22 to 23° C. for 2 hours. After the reaction was completed, the resultant reaction liquid was subjected to a quantitative analysis using a high performance liquid chromatography. In the result, the target 1-acetoxy-2-methyl-3-(3,4-dimethoxyphenyl)propene was obtained in a yield of 94.4% (amount: 2.36 g).

Comparative Example 3

In an argon gas atmosphere, a three necked flask having a capacity of 25 ml was charged with 1.18 g (62 m moles) of titanium tetrachloride and then with 0.016 g (0.11 m mol) of boron trifluoride ether complex. Into the mixture, 3.40 g (24.6 m moles) of 1,2-dimethoxybenzene were added dropwise at an internal temperature of 8 to 12° C. for 30 minutes and thereafter a mixture of 0.96 g (5.6 ml) of 3,3-diacetoxy-2-methylpropene having a purity degree of 100% by mass and 0.77 g (5.6 m moles) of 1,2-dimethoxybenzene were added dropwise for 5 minutes. The resultant mixture was stirred at an internal temperature of 8 to 10° C. for 60 minutes, and then the resultant mixture was mixed with 10 ml of a 6N hydrochloric acid and 10 ml of dichloromethane, and stirred for 30 minutes. The resultant reaction liquid was filtered to remove a insoluble fraction from the reaction liquid. The filtrate was extracted with dichloromethane, the resultant organic layer was washed with water, then with a saturated aqueous sodium chloride solution, and dried over Na$_2$SO$_4$. The resultant reaction liquid was filtered, the resultant filtrate was concentrated. A crude product was obtained in an amount of 4.54 g. The crude product was subjected to a quantitative analysis using a high performance liquid chromatography. As a result, it was found that the target 1-acetoxy-2-methyl-3-(3,4-dimethoxyphenyl)propene was obtained in a yield of 12% (amount: 0.18 g).

The resultant product had a brown color and by an analysis using the high performance liquid chromatography, a plurality of by-products were confirmed to be contained in the product.

Example 17

In an argon gas atmosphere, a three necked flask having a capacity of 100 ml was charged with 1.86 g (3 m moles) of ytterbium triflate (ytterbium trifluoromethanesulfonate) and then with 61.38 g (502.6 m moles) of 1,2-methylenedioxybenzene. The mixed liquid in the flask was mixed with 19.30 g (100.0 m moles) of 3,3-diacetoxy-2-methylpropene having a purity degree of 89.2% by mass at an internal temperature of 38 to 40° C. for 30 minutes. The resultant mixed liquid was stirred at an internal temperature of 40 to 41° C. for 3 hours. The resultant reaction mixed liquid was washed three times with 16 ml of water, and after each washing step was completed, the wasted washing water was evaporated to dryness to recover ytterbium triflate. Separately, the water-washed organic fraction of the reaction liquid was subjected to a quantitative analysis using a high performance liquid chromatography. It was found that the target 1-acetoxy-2-methyl-3-(3,4-methylenedioxyphenyl) propene was obtained in an amount of 19.57 g in an yield of 83.6%.

Example 18

In an argon gas atmosphere, a three necked flask having a capacity of 25 ml was charged with 3.44 g (17.8 m moles) of 3,3-diacetoxy-2-methylpropene having a purity degree of 89.2% by mass and 12.2 g (100.0 mmole) of 1,2-methylenedioxybenzene. Then, the resultant mixture was mixed with 0.23 g (0.6 m mole) of ytterbium trichloride hexahydrate at an internal temperature of 39° C. The resultant reaction mixture was stirred at an internal temperature of 39 to 40° C. for 3 hours.

The resultant reaction liquid was diluted with acetonitrile and subjected to a quantitative analysis using a high performance liquid chromatography. It was found that the target 1-acetoxy-2-methyl-3-(3,4-methylenedioxyphenyl)propene was obtained in an amount of 3.89 g in a yield of 93.1%.

Example 19

In an argon gas atmosphere, a three necked flask having a capacity of 25 ml was charged with 3.86 g (20.0 m moles) of 3,3-diacetoxy-2-methylpropene having a purity degree of 89.2% by mass and 12.212 g (100.0 m moles) of 1,2-methylenedioxybenzene. Then, the resultant mixture was mixed with 0.37 g (0.6 m mole) of ytterbium triflate (recovered in Example 17) at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1-acetoxy-2-methyl-3-(3,4-methylenedioxyphenyl)propene was obtained in an amount of 3.64 g in a yield of 77.7%.

Example 20

In an argon gas atmosphere, a three necked flask having a capacity of 25 ml was charged with 3.86 g (20.0 m moles) of 3,3-diacetoxy-2-methylpropene having a purity degree of 89.2% by mass and 12.21 g (100.0 m moles) of 1,2-methylenedioxybenzene. Then, the resultant mixture was mixed with 0.25 g (0.6 m mole) of tin triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1-acetoxy-2-methyl-3-(3,4-methylenedioxyphenyl)propene was obtained in an amount of 4.10 g in a yield of 87.6%.

Example 21

In an argon gas atmosphere, a three necked flask having a capacity of 25 ml was charged with 3.86 g (20.0 m moles) of 3,3-diacetoxy-2-methylpropene having a purity degree of 89.2% by mass and 12.21 g (100.0 m moles) of 1,2-methylenedioxybenzene. Then, the resultant mixture was mixed with 0.16 g (0.6 m mole) of tin tetrachloride at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1-acetoxy-2-methyl-3-(3,4-methylenedioxyphenyl)propene was obtained in an amount of 4.15 g in a yield of 88.5%.

Example 22

In an argon gas atmosphere, a three necked flask having a capacity of 25 ml was charged with 3.86 g (20.0 m moles) of 3,3-diacetoxy-2-methylpropene having a purity degree of 89.2% by mass and 12.21 g (100.0 m moles) of 1,2-methylenedioxybenzene. Then, the resultant mixture was mixed with 0.36 g (0.6 m mole) of cerium triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1,-acetoxy-2-methyl-3-(3,4-methylenedioxyphenyl)propene was obtained in an amount of 3.64 g in a yield of 77.7%.

Example 23

In an argon gas atmosphere, a three necked flask having a capacity of 25 ml was charged with 3.86 g (20.0 m moles) of 3,3-diacetoxy-2-methylpropene having a purity degree of 89.2% by mass and 12.21 g (100.0 m moles) of 1,2-methylenedioxybenzene. Then, the resultant mixture was mixed with 0.37 g (0.6 m mole) of dysprosium triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1,-acetoxy-2-methyl-3-(3,4-methylenedioxyphenyl)propene was obtained in an amount of 3.26 g in a yield of 69.6%.

Example 24

In an argon gas atmosphere, a three necked flask having a capacity of 25 ml was charged with 3.86 g (20.0 m moles) of 3,3-diacetoxy-2-methylpropene having a purity degree of 89.2% by mass and 12.21 g (100.0 m moles) of 1,2-methylenedioxybenzene. Then, the resultant mixture was mixed with 0.37 g (0.6 m mole) of holmium triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1,-acetoxy-2-methyl-3-(3,4-methylenedioxyphenyl)propene was obtained in an amount of 3.56 g in a yield of 76.1%.

Example 25

In an argon gas atmosphere, a three necked flask having a capacity of 25 ml was charged with 3.86 g (20.0 m moles) of 3,3-diacetoxy-2-methylpropene having a purity degree of 89.2% by mass and 12.21 g (100.0 m moles) of 1,2-methylenedioxybenzene. Then, the resultant mixture was mixed with 0.37 g (0.6 m mole) of lutetium triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1,-acetoxy-2-methyl-3-(3,4-methylenedioxyphenyl)propene was obtained in an amount of 3.91 g in a yield of 83.5%.

Example 26

In an argon gas atmosphere, a three necked flask having a capacity of 25 ml was charged with 3.86 g (20.0 m moles) of 3,3-diacetoxy-2-methylpropene having a purity degree of 89.2% by mass and 12.21 g (100.0 m moles) of 1,2-methylenedioxybenzene. Then, the resultant mixture was mixed with 0.370 g (0.6 m mole) of thulium triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1,-acetoxy-2-methyl-3-(3,4-methylenedioxyphenyl)propene was obtained in an amount of 3.89 g in a yield of 82.9%.

Example 27

In an argon gas atmosphere, a three necked flask having a capacity of 25 ml was charged with 3.86 g (20.0 m moles) of 3,3-diacetoxy-2-methylpropene having a purity degree of 89.2% by mass and 12.21 g (100.0 m moles) of 1,2-methylenedioxybenzene. Then, the resultant mixture was mixed with 0.37 g (0.6 m mole) of erbium triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1,-acetoxy-2-methyl-3-(3,4-methylenedioxyphenyl)propene was obtained in an amount of 3.77 g in a yield of 80.5%.

Example 28

In an argon gas atmosphere, a three necked flask having a capacity of 25 ml was charged with 3.86 g (20.0 m moles) of 3,3-diacetoxy-2-methylpropene having a purity degree of 89.2% by mass and 10.82 g (100.0 m moles) of anisol. Then, the resultant mixture was mixed with 0.22 g (0.6 m mole) of copper triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1,-acetoxy-2-methyl-3-(4-methoxyphenyl)propene was obtained in an amount of 4.09 g in a yield of 92.7%.

Example 29

In an argon gas atmosphere, a three necked flask having a capacity of 25 ml was charged with 3.86 g (20.0 m moles) of 3,3-diacetoxy-2-methylpropene having a purity degree of 89.2% by mass and 11.0 g (101.8 m moles) of anisol. Then, the resultant mixture was mixed with 0.37 g (0.6 m mole) of ytterbium triflate at an internal temperature of 38° C. The mixture was stirred at an internal temperature of 39 to 40° C. for 3 hours.

The resultant reaction liquid was diluted with acetonitrile and subjected to a quantitative analysis using a high performance liquid chromatography. It was found that the target 1,-acetoxy-2-methyl-3-(4-methoxyphenyl)propene was obtained in an amount of 4.15 g in a yield of 94.2%.

Example 30

In an argon gas atmosphere, a three necked flask having a capacity of 25 ml was charged with a mixture of 7.04 g (51.7 m moles) of 1,2-ethylenedioxybenzene having a purity degree of 97% by mass with 0.97 g (5.0 m moles) of 3,3-diacetoxy-2-methylpropene having a purity degree of 89.2% by mass, and then the mixture was further mixed with 71 mg (0.5 m mole) of boron trifluoride-ether complex at an internal temperature of 24° C. The mixture was stirred at an internal temperature of 24° C. for 2 hours.

The resultant reaction liquid was mixed with 50 ml of ethyl acetate, and the resultant organic layer was washed twice with 50 ml of water and dried over anhydrous sodium sulfate, and the solvent was removed by distillation. The distillation residue was subjected to a column chromatography on silica gel and treated with an eluting solvent: ethyl acetate/n-hexane mixture in a mixing ratio by volume of 1/5. The target 1-acetoxy-2-methyl-3-(3,4-ethylenedioxyphenyl) propene in an oily state was obtained in an amount of 0.97 g. The isolation yield of the target compound was 78.2%.

The physical property data of 1-acetoxy-2-methyl-3-(3, 4-ethylenedioxyphenyl)propene are shown below.

$^1$H-NMR (300 MHz, CDCl$_3$) δ:1.59 (3H, d, J=1.5 Hz), 2.14 (3H, s), 3.15 (2H, s), 4.23 (4H, s), 6.64 (1H, dd, J=8.1 Hz, J=2.0 HZ), 6.69 (1H, d, J=2.0 Hz), 6.77 (1H, d, J=8.1 Hz), 7.02 (1H, q, J=1.5 Hz).

HRMS (EI)(M+)

Calculated for $C_{14}H_{16}O_4$: 248.1049.

Found: 248.1051.

INDUSTRIAL APPLICABILITY

The process enables a 1-acetoxy-3-(substituted phenyl) propene compound useful, as an intermediate, for perfumes, pharmaceutical chemicals, agricultural chemicals and other organic synthetic chemicals, to be easily produced in a high yield. Thus the process for producing 1-acetoxy-3-(substituted phenyl)propene compounds has a high applicability in industry. Also, the 1-acetoxy-3-(substituted phenyl)propene compounds produced by the process include new compounds.

What is claimed is:

1. A process for producing a 1-acetoxy-3-(substituted phenyl) propene compound represented by the general formula (I):

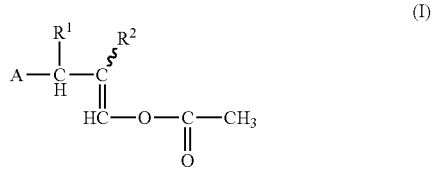

in which formula (I), $R^1$ and $R^2$, respectively and independently from each other, represented a member selected from the groups consisting of a hydrogen atom and alkyl groups having 1 to 10 carbon atoms, $R^1$ and $R^2$ may form, together with carbon atoms located in the 2- and 3-positions of the propene group, a cyclic group; and A represents a member selected from a group of substituted phenyl groups represented by the formulae (II) and (III):

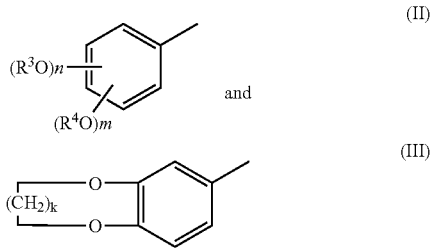

wherein $R^3$ and $R^4$, respectively and independently from each other, represent an alkyl group having 1 to 4 carbon atoms, m represents an integer of 0 or 1 to 4, n represents an integer of 1 or 5 and k represents an integer of 1 or 2, comprising reacting a benzene compound selected from those represented by the general formulae (IV) and (V):

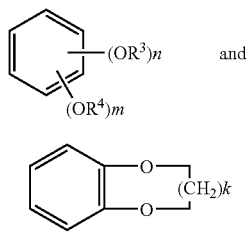

(IV)

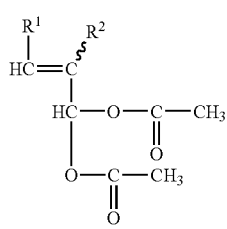

(V)

in which formula (IV) and (V), $R^3$ and $R^4$ and n, m and k are as defined above, with a 2-alkenylidene diacetate compound represented by the general formula (VI):

$$\begin{array}{c} R^1 \quad R^2 \\ | \quad | \\ HC{=}C \\ | \\ HC{-}O{-}C{-}CH_3 \\ | \quad \quad \| \\ \quad \quad O \\ O{-}C{-}CH_3 \\ \| \\ O \end{array}$$

(VI)

in which formula (VI), $R^1$ and $R^2$ are as defined above, in the presence of a catalyst consisting essentially of at least one compound selected from the group consisting of (a) halogenated boron compounds, (b) triflate compounds of Group 11 elements of the Periodic Table, (c) halogenated compounds of Group 12 elements of the Periodic Table, and (d) triflate compounds and halogenated compounds of tin and lanthanoid elements of atomic numbers 58 and 66 to 71.

2. The process for producing a 1-acetoxy-3-(substituted phenyl)propene compound as claimed in claim 1, wherein the benzene compounds represented by the formula (IV) is selected from the group consisting of anisole, veratrol, hydroquinone dimethylether, pyrogallol trimethylether and hydroxyhydroquinone trimethylether.

3. The process for producing a 1-acetoxy-3-(substituted phenyl)propene compound as claimed in claim 1, wherein the benzene compounds represented by the formula (V) is selected from the group consisting of 1,2-methylenedioxybenzene and 1,2-ethylenedioxybenzene.

4. The process for producing a 1-acetoxy-3-(substituted phenyl)propene compound as claimed in claim 1, wherein the alkenylidene diacetate is selected from the group consisting of 3,3-diacetoxy-1-methylpropene, 3,3-diacetoxy propene, 3,3-diacetoxy-1-methylpropene, 3,3-diacetoxy-2-ethyl propene, 3,3-diacetoxy-1-ethylpropene, and 3,3-diacetoxy-1-ethyl-2-methylpropene.

5. The process for producing a 1-acetoxy-3-(substituted phenyl)propene compound as claimed in claim 1, wherein the reaction is carried out in a molar ratio of the benzene compound to the alkenylidene diacetate compound of 1:1 to 50:1.

6. The process for producing a 1-acetoxy-3-(substituted phenyl)propene compound as claimed in claim 1, wherein the catalyst is present in an amount of 0.005 to 1 mole per mole of the alkenylidene diacetate compound.

7. The process for producing a 1-acetoxy-3-(substituted phenyl)propene compound as claimed in claim 1, wherein the halogenated boron compounds (a) usable for the catalyst are selected from boron fluorides, boron trifluoride-diethylether complexes, borontrifluoride-tetrahydrofuran complexes, boron trifluoride-acetic acid complex salt, boron trifluoride dehydrate, and boron trifluoride-n-buthylether complexes.

8. The process for producing a 1-acetoxy-3-(substituted phenyl)propene compound as claimed in claim 1, wherein the triflate compounds (b) of Group 11 elements of the Periodic Table usable for the catalyst are selected from the group consisting of copper triflate and silver triflate.

9. The process for producing a 1-acetoxy-3-(substituted phenyl) propene compound as claimed in claim 1, wherein the halogenated compounds (c) of Group 12 elements usable for the catalyst are selected from the group consisting of zinc fluoride, zincchloride, zinc bromide, zinc iodide, cadmium fluoride, cadmium chloride, cadmium bromide, cadmium iodide, mercury fluoride, mercury chloride, mercury bromide, and mercury iodide.

10. The process for producing a 1-acetoxy-3-(substituted phenyl) propene compound as claimed in claim 1, wherein the triflate and halogenated compounds (d) of tin and lanthanoid elements of atomic numbers 58 and 66 to 71 are selected from the group consisting of triflates, fluorides, chloride, bromides, and iodide of tin, cerium, dysprosium, holmium, erbium, thulium, ytterbium and lutetium.

11. The process for producing a 1-acetoxy-3-(substituted phenyl)propene compound as claimed in claim 1, wherein the reaction is carried out in an atmosphere consisting of a nonreactive gas to the above-mentioned compounds of the formulae (IV), (V) and (VI), the above-mentioned catalyst and the resultant reaction products.

12. The process for producing a 1-acetoxy-3-(substituted phenyl)propene compound as claimed in claim 1, wherein the compounds of the formula (I) are selected from the compounds represented by the general formula (VII):

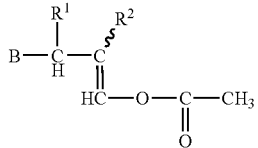

(VII)

in which formula (VII), $R^1$, $R^2$ are as defined above, B represents a member selected from a group of substituted phenyl groups represented by the formulae (VIII) and (IX):

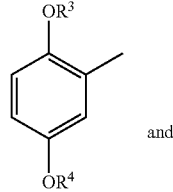

(VIII)

and

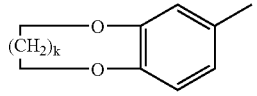

(IX)

in which formulae (VIII) and (IX), $R^3$ and $R^4$ and k are as defined above.

13. The process for producing a 1-acetoxy-3-(substituted phenyl) propene compound as claimed in claim 1, wherein the compound of the formula (I) is selected from 1-acetoxy-3-(3,4-C1 to C2 alkylene dioxyphenyl)propenes represented by the formulae (X) and (XI):

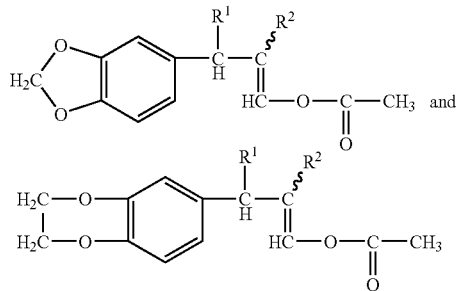

in which formulae (X) and (XI), $R^1$ and $R^2$ are as defined above.

14. The process for producing a 1-acetoxy-3-(substituted phenyl)propene compound as claimed in claim 12, wherein in the formulae (X) and (XI), $R^1$ represents a hydrogen atom and $R^2$ represents a methyl group.

15. The process for producing a 1-acetoxy-3-(substituted phenyl)propene compound as claimed in claim 1, wherein the compound of the formula (I) is selected from the groups consisting of 1-acetoxy-2-methyl-3-(3,4-methylenedioxyphenyl)propene, 1-acetoxy-2-methyl-3-(3,4-ethylenedioxyphenyl)propene, 1-acetoxy-2-methyl-3-(4-methoxyphenyl)propene, 1-acetoxy-2-methyl-3-(2,5-dimethoxyphenyl)propene, and 1-acetoxy-2-methyl-3-(3, 4-dimethoxy-phenyl)propene.

* * * * *